United States Patent [19]

Weissenbacher et al.

[11] Patent Number: 5,305,633
[45] Date of Patent: Apr. 26, 1994

[54] HARDNESS TESTER INCLUDING A FORCE GAGE FOR MEASURING THE FORCE EXERTED SO AS TO CONTROL THE DRIVE UNIT

[75] Inventors: Herbert Weissenbacher; Karl Brutmann, both of Salzburg, Austria

[73] Assignee: EMCO Maier Gesellschaft mbH, Austria

[21] Appl. No.: 623,358

[22] Filed: Dec. 7, 1990

[30] Foreign Application Priority Data

Dec. 7, 1989 [AT] Austria .................................. 2786/89

[51] Int. Cl.⁵ .............................................. G01N 3/42
[52] U.S. Cl. .................................................. 73/82
[58] Field of Search ............................... 73/81, 82, 83

[56] References Cited

U.S. PATENT DOCUMENTS

| | | | |
|---|---|---|---|
| 2,109,521 | 3/1938 | Ballentine | 73/82 |
| 2,224,936 | 12/1940 | Smith | 73/83 |
| 2,491,667 | 11/1945 | Kent | 73/81 |
| 2,564,519 | 8/1951 | Bergsman | 73/81 |
| 2,752,779 | 7/1956 | Clark | 73/83 |
| 2,850,894 | 9/1958 | Clark | 73/83 |
| 2,892,344 | 6/1959 | Sklar | 73/83 |
| 3,119,255 | 1/1964 | Akashi et al. | 73/83 |
| 3,468,159 | 5/1967 | Loomie | 73/81 |
| 3,855,848 | 12/1974 | Sidler | 73/81 |
| 3,949,600 | 4/1976 | Iwasaki | 73/83 |
| 4,094,188 | 6/1978 | Bellouin et al. | 73/81 |
| 4,118,975 | 10/1978 | Iwasaki | 73/81 |
| 4,136,555 | 1/1979 | Iwasaki | 73/83 |
| 4,157,655 | 6/1979 | Campbell et al. | 73/81 |
| 4,611,487 | 9/1986 | Krenn et al. | 73/81 |

FOREIGN PATENT DOCUMENTS

| | | | |
|---|---|---|---|
| 48801 | 1/1988 | Australia | 73/82 |
| 383423 | 7/1987 | Austria . | |
| 8121192 | 6/1981 | Fed. Rep. of Germany . | |
| 3710741 | 3/1987 | Fed. Rep. of Germany . | |
| 8800691 | 1/1988 | PCT Int'l Appl. | 73/82 |
| 405761 | 7/1966 | Switzerland . | |

Primary Examiner—Hezron E. Williams
Assistant Examiner—Nashmiya Ashraf
Attorney, Agent, or Firm—Feiereisen & Kueffner

[57] ABSTRACT

A hardness tester includes an indentor which is mounted to a linearly guided carrier movably supported in a frame, with a linkage mechanism being attached to the carrier for transmitting the load onto the indentor. Interposed within the linkage mechanism is a force gage which converts the force exerted thereupon into an electric variable and is operatively connected to a comparator circuit by which the electric variable generated in the force gage is compared with a preset, selectable desired value. The comparator circuit includes an output which controls a drive unit which in turn is connected to the linkage mechanism by which the load upon the indentor is exerted.

11 Claims, 4 Drawing Sheets

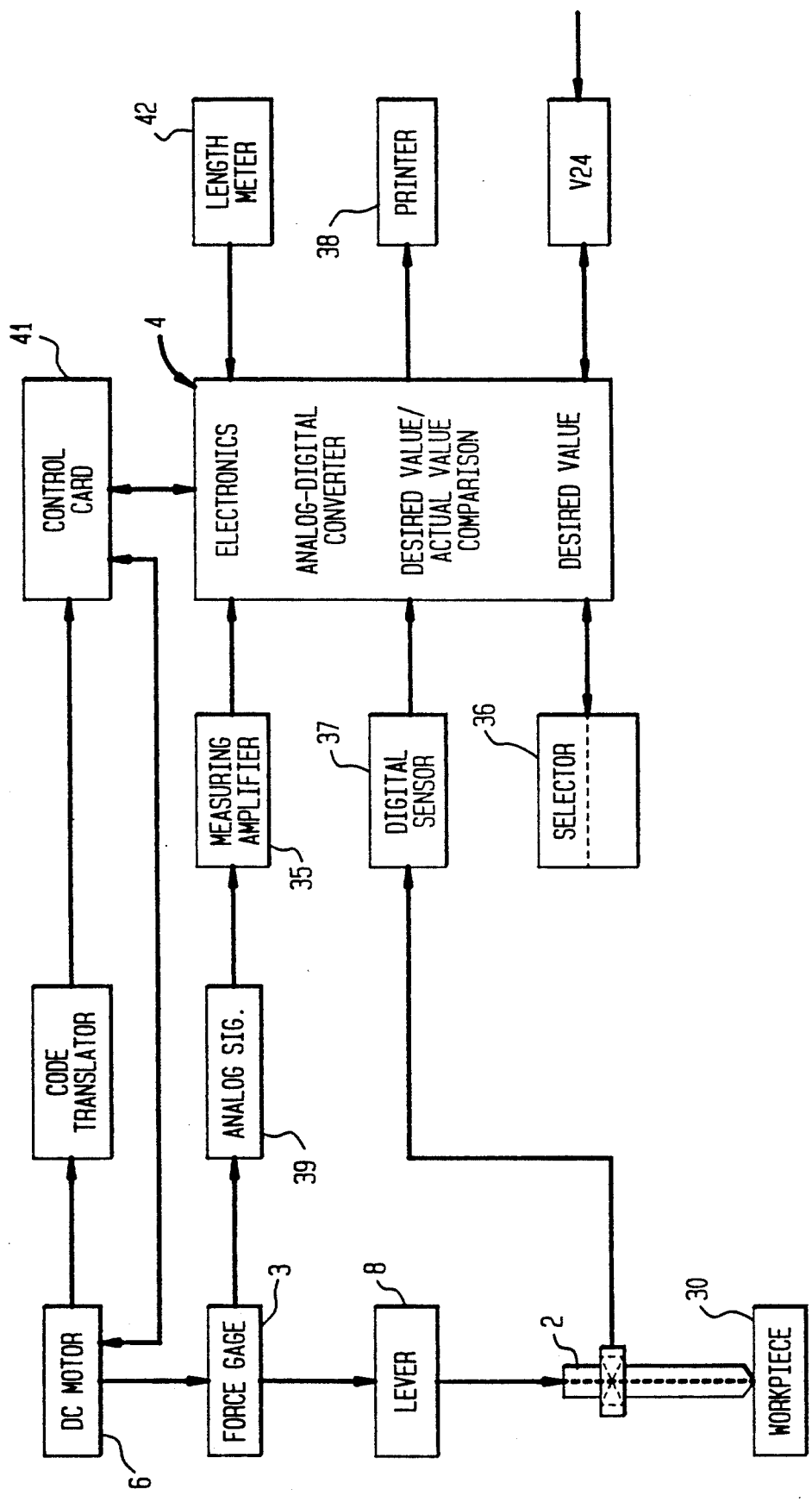

HARDNESS TESTER INCLUDING A FORCE GAGE FOR MEASURING THE FORCE EXERTED SO AS TO CONTROL THE DRIVE UNIT

BACKGROUND OF THE INVENTION

The present invention refers to a hardness tester, and in particular to a hardness tester of the type having an indentor which is mounted to a linearly guided carrier movably supported in a frame, with a linkage mechanism being attached to the carrier for transmitting the load onto the indentor.

Hardness tests may be carried out with or without preliminary force. Depending on the type of testing method, balls, pyramids, cones and also double cones (Grodzinski, Buchholz) may be used as indentors.

Conventional hardness testers are very complicated and require cumbersome handling when it comes to attachment of loads with weights, the use of additional weights in preliminary hardness testing methods or the attenuation of the movement by providing oil brakes.

SUMMARY OF THE INVENTION

It is thus an object of the present invention to provide an improved hardness tester obviating the afore-stated drawbacks.

This object, and others which will become apparent hereinafter are attained in accordance with the present invention by accommodating within the linkage mechanism a force gage which converts the force exerted thereupon into an electric variable and is operatively connected to a comparator circuit by which the electric variable generated in the force gage is compared with a selectable desired value, with the output of the comparator circuit controlling a drive unit which is connected to the linkage mechanism by which a load is transmitted upon the indentor.

Preferably, the drive unit includes a motor and a transmission with high reduction ratio, in particular with a reduction ratio of 1:900.

Through integration of the force gage within the linkage mechanism, the actual load exerted by the indentor can be ascertained and the load can be constantly modified by the drive unit via the comparison of actual value and desired value.

A hardness tester according to the invention can be employed in every incoming inspection, production inspection, laboratory, inspection, hardening shop, foundry, smithery and training center.

Testing methods according to Vickers, Rockwell, Brinell as well as for plastics according to DIN 51224, 51225, 50103, 50351 and 53456 can be carried out. Also loads other than those set forth can easily be accomplished.

According to a further feature of the present invention, the linkage mechanism includes a lever which is swingably mounted in the frame and connected to the carrier, with the force gage having one end mounted to the lever and another end connected to a swingable coupler which is driven via a crank or eccentric member by the motor of the drive unit. The lever defines with the frame coupler and the eccentric member a four-bar linkage. Suitably, the four-bar linkage is arranged in such a manner that the coupler is oriented approximately vertical. During operation, the coupler oscillates about the point of application of the lever for the carrier of the indentor.

Preferably, the lever is forked to define a forked part which encloses the carrier and accommodates two rollers which preferably oppose each other and engage respective recesses of the carrier. An engagement sleeve is slipped on the carrier and provided with a circular groove which defines the recesses.

For determining the indentation of the indentor, it is suitable to provide a sensor which is supported by the carrier, on the one hand, and by the frame, on the other hand.

BRIEF DESCRIPTION OF THE DRAWING

The above and other objects, features and advantages of the present invention will now be described in more detail with reference to the accompanying drawing in which:

FIG. 6 is a schematic block diagram showing various nonmechanical parts of a comparator circuit for a hardness tester in accordance with the present invention.

DETAILED DESCRIPTION OF PREFERRED EMBODIMENTS

Figure 1:
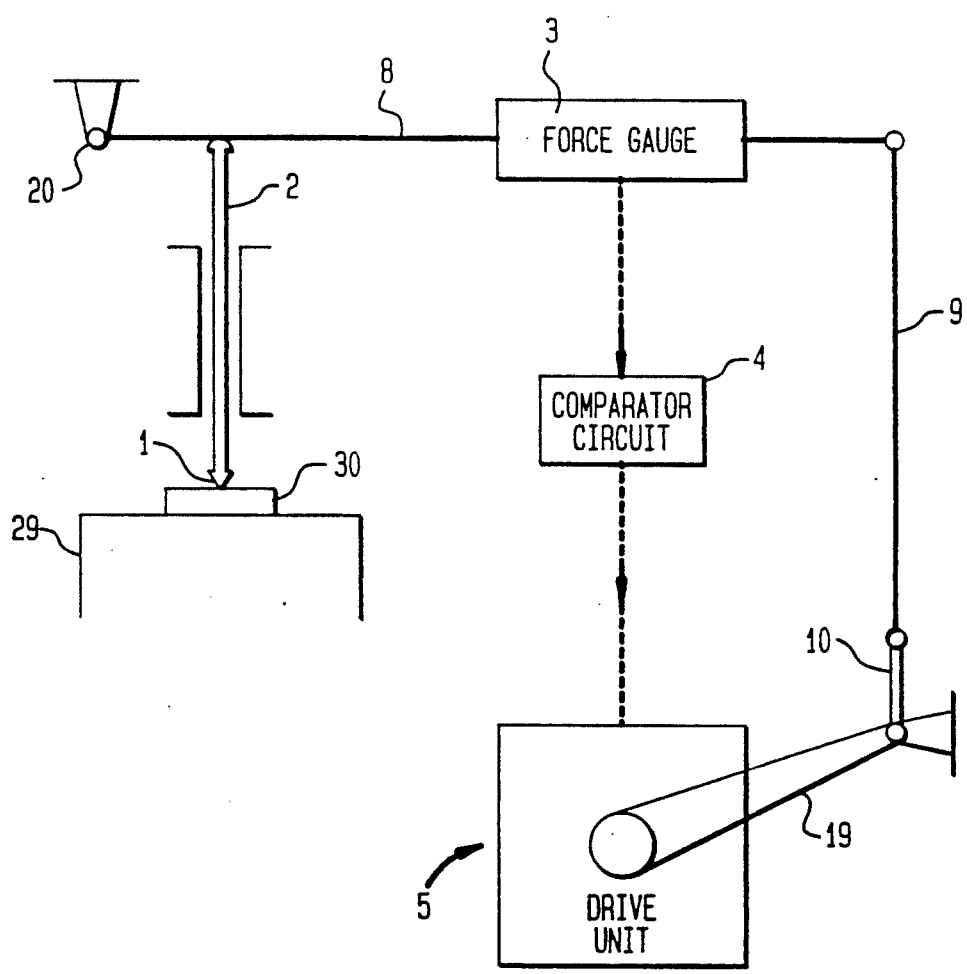
FIG. 1 is a schematic illustration of one embodiment of a hardness tester in accordance with the invention, showing generally the structure of a hardness tester in accordance with the invention.

Throughout all the Figures, the same or corresponding elements are always indicated by the same reference numerals.

Turning now to FIG. 1, there is shown a schematic illustration of one embodiment of a hardness tester in accordance with the invention, depicting a general overall view of the elements of the hardness tester. The hardness tester includes an indentor 1 which is securely, but preferably exchangeably, mounted to a carrier 2. The carrier 2 is movably mounted and preferably linearly guided within a frame 32. A linkage mechanism 8, 9, 10, which will be described in more detail hereinafter, is operatively connected to the carrier 2 for transmitting the load onto the indentor 1. Accommodated within the linkage mechanism is a load receiving and transmitting element in form of a force gage 3 which is a conventional element such as e.g. a force gage made available by the company Hottinger Baldwin Messtechnik Gmbh, Darmstadt, Germany. Such a force gage includes a load transmitting and receiving element of highly quenched and tempered steel which is provided with strain foils. A bellows of high-grade steel is soldered on to protect the strain foils from external influences. The measuring element has a nickel-plated surface and includes a twin bending beam, with its one end being clamped and with its other free end being subjected to the tensile load or pressure load. The load exerted upon the force gage 3 is converted into an analog electric signal. When designing the force gage in form of a load cell, the calibration is provided in the unit of mass "kilogram", with consideration of the acceleration due to gravity. When required, the force gage may also be calibrated in the unit of force "newton".

The force gage 3 is electrically connected to a comparator circuit 4 by which the electric value generated in the force gage 3 is compared with a preset, selectable desired value. The output of the comparator circuit 4 controls the drive unit 5 for the linkage mechanism, with the drive unit 5 preferably including a d.c. motor 6 and a transmission 7 with high gear ratio, e.g. 1:900. Persons skilled in the art will recognize that the drive unit is shown by way of example only, and may be substituted by another suitable drive unit, such as for example a hydraulic piston/cylinder unit. Thus by comparing the force exerted upon the force gage with a desired reference value, the load acting upon the indentor 1 can be continuously adjusted by operating the motor 6 which in turn actuates the linkage mechanism 8, 9, 10.

Figure 2:
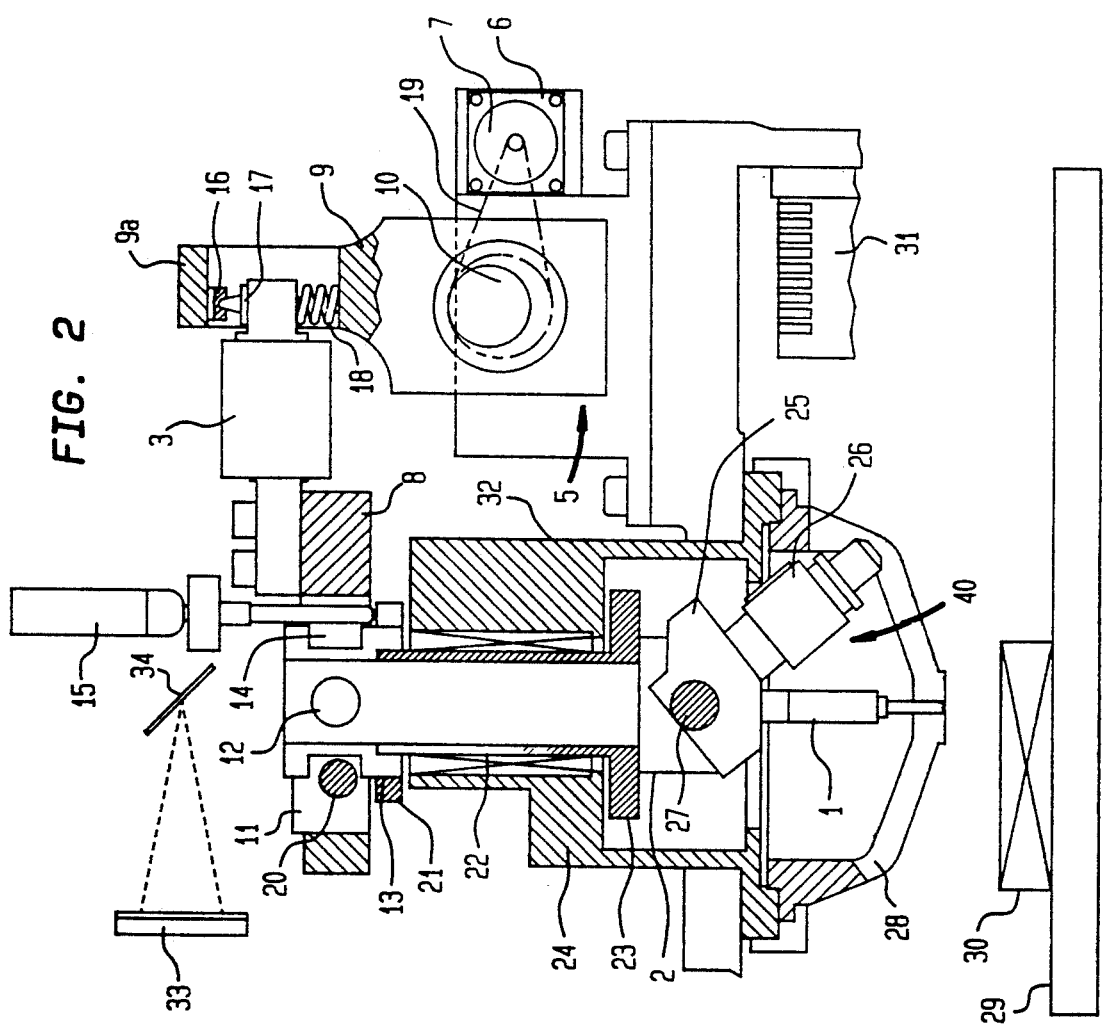
FIG. 2 shows a detailed illustration, partly sectional, of a hardness tester in accordance with the present invention.

Turning now to FIGS. 2 to 5, and in particular to FIG. 2, there is shown an exemplified illustration, partly sectional, of a hardness tester in accordance with the present invention, with its individual parts shown in detail. Mounted to the carrier 2 of the indentor 1 within the frame 32 of the hardness tester is a lever 8 which is part of the linkage mechanism and swings about pivot 20 which extends at a lateral distance to the carrier 2. Fixedly secured to the lever 8 is one axial end of the force gage 3. The linkage mechanism further includes a coupler 9 which is swingably mounted to the other axial end of the force gage 3 and accommodates a rotating eccentric 10. The eccentric 10 is operatively connected via a toothed belt 19 to the transmission 7 of the d.c. motor 6 so as to allow an oscillating motion of the coupler 9. By means of the toothed belt 19, a reduction ratio of 1:10 is attained. Suitably, the drive motor 6 may be a four watts d.c. motor with pulse generator (500 pulses per revolution). It will be recognized that instead of the eccentric 10, the actuation of the coupler 9 may also be attained via a crank.

Figure 3:
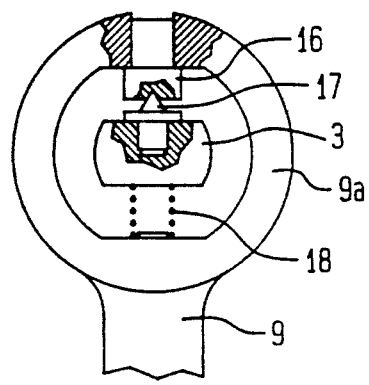
FIG. 3 is a side view, partly sectional, of the hardness tester of FIG. 2, showing in detail the upper end of the coupler which is an element of the linkage mechanism.

As can be seen in particular in FIGS. 2 and 3, the coupler 9 has an upper forked extension 9a which receives the force gage 3 via a cone bearing. The cone bearing includes a socket 16 which has a cone angle of preferably 90° and is engaged by a cone 17 having a cone angle being smaller than the cone angle of the socket 16. The angle of the cone 17 may be, for example 60°. The cone 17 is securely fixed to the force gage 3 and is urged into the socket 16 by two tension springs 18 which are supported in the forked extension 9a precisely in the plane defined through the apex of the cone 17, as can be seen from FIG. 2.

The lever 8, the coupler 9 and the eccentric 10 (or crank) are part of a four-bar linkage, with the stationary frame 32 representing the fourth link.

Figure 4:
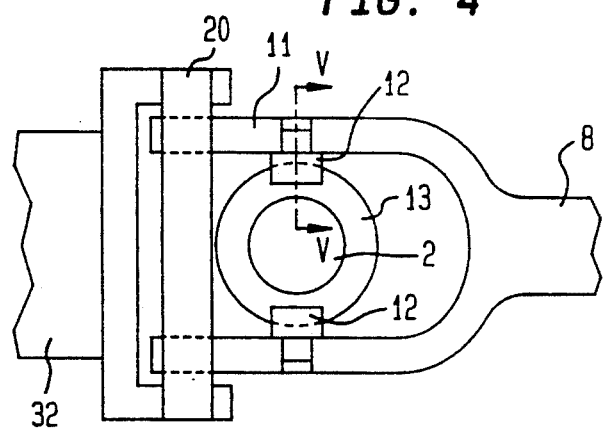
FIG. 4 is a plan view of the hardness tester of FIG. 2, showing in detail the forked part of the lever which is another element of the linkage mechanism.
Figure 5:
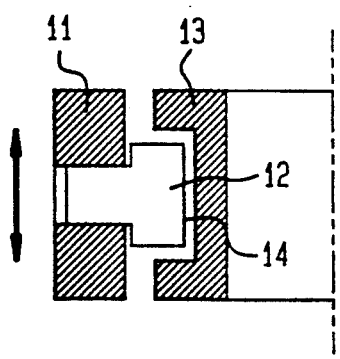
FIG. 5 is a cross sectional view through one prong of the forked part, taken along the line V—V in FIG. 4.

As can be seen in particular in FIGS. 2 and 4, the swingably mounted lever 8, by which the carrier 2 of the indentor 1 is loaded, is of fork-like configuration, with the fork section 11 surrounding the carrier 2. Arranged in the fork section 11 are two rollers 12 (FIG. 4) which preferably oppose each other and engage respective recesses of the carrier 2. Preferably, the recesses are defined by a circular groove 14 which is provided in an engagement sleeve 13 as shown in particular in FIG. 5. The engagement sleeve 13 is slipped on the carrier 2 and fixed thereto. Persons skilled in the art will understand that the rollers are shown by way of example only. Other engaging members such as pins or the like may be used as well. However, in view of their low friction, the use of rollers is preferred.

FIG. 2 shows that the point of application of the coupler 9 to the force gage 3 is distanced from the pivot 20 of the lever 8 by six units while the point of application of the rollers 12 to the carrier 2 for the indentor 1 is distanced from the pivot 20 by one unit. Thus, the gear ratio at the lever 8 is 6:1.

As further shown in FIG. 2, the engagement sleeve 13 is provided with a circumferential collar 21 by which the lower end of a sensor 15 is supported. By means of the sensor 15, the indentation of the indentor 1 is determined. Surrounding a major portion of the carrier 2 is a guide sleeve 22, with its upper end projecting into a circular recess of the engagement sleeve 13 and with its lower end, which faces the indentor 1, being provided with a flange 23. The flange 23 bears upon a shoulder of the carrier 2 and is provided with a pin 24 which parallels the axis of the carrier 2 and projects into the frame 32 so as to prevent the carrier 2 from being deflected or tilted from its straight alignment.

At its lower end, the carrier 2 is provided with a microscope generally designated by reference numeral 40 for providing an image of the indentation in a workpiece or specimen 30. The microscope 40 includes a revolving nosepiece 25 and a microscope objective 26 which is angled relative to the indentor 1. The nosepiece 25 carries the indentor 1 and is swingably mounted about pivot 27 to the carrier 2.

Securely mounted to the lower end of the frame 32 is a testing head 28 by which the indentor 1 and the objective 26 is protected. Below the testing head 28 is a table 29 upon which the workpiece 30 to be tested is placed. Suitably, the table 29 is continuously adjustable in height i.e. its position relative to the indentor 1 is adjustable. For illumination, a halogen lamp 31 is mounted to the frame 32 of the hardness tester. Suitably, the objective 26 is detachably secured to the nosepiece 25 in a same manner as the indentor 1.

The image which is provided by the microscope 40 of the indentation in the workpiece 30 can be projected after deflection by a mirror 34 onto a ground glass screen 33, e.g. at a diameter of 150 mm, in twentyfold, fortyfold, ninety-fivefold, one hundredfold and three hundredfold magnification.

After describing the individual parts of the hardness tester according to the invention, its mode of operation will now be described with inclusion of FIG. 6 which depicts a schematic block diagram showing various nonmechanical parts a comparator circuit for the hardness tester in accordance with the present invention.

Upon carrying out the testing, the table 29 with the workpiece 30 placed thereon is moved upwards towards the testing head 28. The indentor 1 is in its initial position in which it extends about 0.3 mm behind the plane defined by the testing head 28 so that after travelling 0.5 mm after reaching the plane of the testing head 28, the indentor 1 impacts the workpiece 30 for the first time. The upward movement of the table 29 is stopped and an impulse is triggered for initiating the hardness test. Impacting of the indentor 1 upon the workpiece 30 causes a load in the force gage 3. For amplification of the signals outputted by the force gage 3 to the comparator circuit 4, a so-called d.c. measuring amplifier card is applied. Such a card may be used for measuring static variables as well as changing variables whereby the frequency of the variations may range up to 10 kHz. The control range of the d.c. measuring amplifier card ranges from 0 to 10 V. The value "zero" corresponds to a nominal load of 0 kg, and the value "10 volt" corresponds to a nominal load of 50 kg. The linearity deviation over the range from 0 to 10 V amounts to only 0.01%. When taking into consideration that the lever 8 provides a transmission ratio of 1:6 and that the desired voltage is 10 V=50 kg, a maximum force of 300 kg may be exerted by the indentor 1. For different testing methods which may require smaller loads, e.g. hardness Rockwell C=150 kg corresponding to a value of 5 V, a suitable electronic control system may be employed to allow respective selection.

The following description of the operation refers to the testing method HVT15 i.e. to a Vickers indentor with a desired load of 15 kg. The selection of the testing method is made by a selector 36 (FIG. 6) which allows also input of other parameters such as statistics, counter, memory, bar graphics, times, tolerances, translations, correction factors, modes of operation etc., preferably in form of code bars. A desired voltage of 0.5 V, which corresponds to a desired load of 15 kg, is preset. After clamping the workpiece 30 between the testing head 28 and the table 29 and stopping the movement of the table 29, the motor 6 is started by which the belt 19 is driven via the transmission 7 with a reduction ratio of 1:900. The belt 19, which has a reduction ratio of 1:10, rotates the eccentric 10 in clockwise direction so that the coupler 9 oscillates downwards to thereby swing the lever 8 about pivot 20. The swinging of the lever 8 causes the carrier 2 and the indentor 1 to linearly move downwards. After the indentor 1 impacts the workpiece 30, the force gage 3 sends, preferably in form of an analog signal 39, via the measuring amplifier 35 to the comparator circuit 4 a certain voltage signal which remains below 0.5 V. The motor 6 with the pulse generator, which is controlled by the comparator circuit 4, runs until the voltage of 0.5 V, which corresponds to a load of 15 kg, is attained. The flowing or creeping of the material requires a constant readjustment over a freely selectable period with regard to the desired voltage because of the drop of the actual voltage so that a load of 15 kg can be maintained. The readjustment is attained via a control card 41 (FIG. 6) which sends pulses to the d.c. motor 6. Actuation of the motor 6 causes a displacement via the coupler 9 and the lever 8 of the carrier 2 of the indentor 1 so that the test load is maintained at a constant level. Through the provision of the motor 6, precise loads between 1 and 300 kg can be maintained at less than one percent deviation. When testing materials of greater hardness, the setting of the desired value is accomplished much faster than during testing materials of smaller hardness.

The maximum travel of the eccentric 10 is dimensioned in such a manner that at maximum desired load even with extremely soft materials, the desired value is received via the force gage 3 (load cell) and measuring amplifier 35. The maximum travel of the indentor 1 beyond the plane of the testing head 28 may amount to about 1.2 mm. The sensor 15, which may be designed as digital sensor 37, represents the pulse generator and has the function to precisely measure the vertically moving system i.e. the travel of the indentor 1 up to ±0.05 μm. This is necessary for the difference measuring method for indentations as specified in DIN 51224 for the Rockwell test in which the workpiece 30 is loaded by an initial minor load of e.g. 10 kg, with this minor load representing the measuring base "zero". After this load of 10 kg, an additional load of 140 kg is exerted so that the overall load acting upon the indentor 1 is 150 kg. After this load of 150 kg, the load is reduced to the initial minor load of 10 kg. The differential amount or graduation of the indention of the indentor 1 between the first and second loads represents the hardness of the material and can be digitally displayed (LCD display) at 36 of the hardness tester according to the invention. For a printout of desired data, including the determined degree of hardness, the comparator circuit 4 may include a printer 38. Further, the circuit 4 may include an interface output V24 (FIG. 6) with software handshaking for parameters, functions and movements. Also, a length meter 42 (FIG. 6) may be operatively connected to the comparator circuit 4. Such a length meter is an incremental displacement pickup which is of the glass scale type and provided for determining the indentation of the indentor.

For controlling the force control unit, there is provided a code translator (encoder). This code translator is a rotary displacement transmitter, producing 500 pulses per revolution of the motor.

It will be recognized that the testing method can be automated in which case up to 1000 tests per hour may be performed.

While the invention has been illustrated and described as embodied in a hardness tester, it is not intended to be limited to the details shown since various modifications and structural changes may be made without departing in any way from the spirit of the present invention.

What is claimed as new and desired to be protected by Letters Patent is set forth in the appended claims:

We claim:

1. A hardness tester comprising
a frame;
a carrier movably guided within said frame;
an indentor connected to said carrier;
linkage means operatively connected to said carrier for transmitting a load upon said indentor, said linkage means including a load receiving and transmitting element in form of a force gage for converting the force generated in said load receiving and transmitting element at impact of said indentor upon said a workpiece into an electric variable;
circuit means electrically connected to said force gage for comparing the electric variable generated in said force gage with a selectable desired value, said circuit means having an output; and
drive means connected to said linkage means and communicating with the output of said circuit means so that said circuit means controls said drive means to thereby control the load exerted upon said indentor via said linkage means;
said linkage means further including a lever movably mounted in said frame and bearing upon said carrier, and a coupler operatively connected to said drive means, said load receiving and transmitting element being interposed between said lever and said coupler.

2. A hardness tester as defined in claim 1 wherein said drive means includes a motor and a transmission with a reduction ratio of 1:900.

3. A hardness tester as defined in claim 1, and further comprising a sensor supported by said carrier for determining the indentation of said indentor in a workpiece.

4. A hardness tester as defined in claim 1, wherein said linkage means further includes a link rotatably connected to said coupler and acted upon by said drive means.

5. A hardness tester as defined in claim 4 wherein said link is a crank.

6. A hardness tester as defined in claim 4 wherein said link is an eccentric.

7. A hardness tester as defined in claim 1 wherein said coupler is swingably mounted to said force gage.

8. A hardness tester as defined in claim 4 wherein said lever is forked to define a forked part surrounding said carrier and accommodating two rollers engaging respective recesses of said carrier.

9. A hardness tester as defined in claim 8, and further comprising an engagement sleeve slipped on said carrier and provided with a circular groove defining said recesses.

10. A hardness tester as defined in claim 8 wherein said rollers oppose each other.

11. A hardness tester comprising a frame;

a carrier movably guided within said frame;

an indentor connected to said carrier;

linkage means operatively connected to said carrier for transmitting a load upon said indentor, said linkage means including a force gage converting the force exerted upon said force gage into an electric variable;

circuit means electrically connected to said force gage for comparing the electric variable generated in said force gage with a selectable desired value, said circuit means having an output; and drive means connected to said linkage means and communicating with the output of said circuit means so that said circuit means controls said drive means to thereby control the load exerted upon said indentor via said linkage means;

said linkage means further including a lever swingably mounted within said frame and connected to said carrier, with said force gage having one end mounted to said lever and another end connected to said drive means via a coupler, wherein said lever is forked to define a forked part surrounding said carrier and accommodating two rollers engaging respective recesses of said carrier.

* * * * *